United States Patent [19]

Bertuch, Jr.

[11] 4,305,394

[45] Dec. 15, 1981

[54] ACETABULAR CUP POSITIONING INSTRUMENT

[76] Inventor: Charles J. Bertuch, Jr., 76 Guy Park Ave., Amsterdam, N.Y. 12010

[21] Appl. No.: 218,563

[22] Filed: Dec. 22, 1980

[51] Int. Cl.³ .............................................. A61B 17/00
[52] U.S. Cl. ............................ 128/303 R; 128/92 R; 128/92 E
[58] Field of Search ............ 128/92 EC, 92 E, 303 R, 128/92 R; 3/1.912, 1.913

[56] References Cited

U.S. PATENT DOCUMENTS

| | | | |
|---|---|---|---|
| 2,905,178 | 9/1959 | Hilzinger | 128/303 R |
| 3,859,992 | 1/1975 | Amstutz | 128/92 E |
| 3,877,433 | 4/1975 | Librach | 128/303 R |

OTHER PUBLICATIONS

Zimmer Catalog, pp. 1 and A34, (1978).
Richards Orthopedic Catalog, Cover Page and pp. 2, 6 and 7, (1969).

*Primary Examiner*—Michael H. Thaler
*Attorney, Agent, or Firm*—Walter F. Wessendorf, Jr.

[57] ABSTRACT

Disclosed is an acetabular prosthetic cup positioning instrument for use in positioning such cup during total hip surgery. The acetabular cup has a convex outer portion that is disposed in the patient's reamed and prepared acetabulum, the cup has an inner cavity and the cup has a rearward-most portion between such outer portion and inner cavity defining a rim portion. The instrument has an interchangeable ball and flange for respective engagement with such cup's inner cavity and rim portion to mount, orient and align such cup relative to such instrument. A drive mechanism, operatively connected through a drive coupling rod, flexible drive cable and drive member and carrying such ball, effects translatory movement of such ball away from such flange while such ball maintains its engagement with such cup's inner cavity to thereby disengage such flange away from such cup's rim portion.

Also disclosed is an interchangeable ball and flange for use with an instrument for positioning an acetabular prosthetic cup of a particular size and type during total hip surgery. Such interchangeable ball and flange mounts, orients and aligns a particular size and type of cup relative to such instrument. Such interchangeable ball and flange can be replaced by another interchangeable ball and flange of a different, particular size and type to mount, orient and align an acetabular cup of such correspondingly different, particular size and type.

25 Claims, 13 Drawing Figures

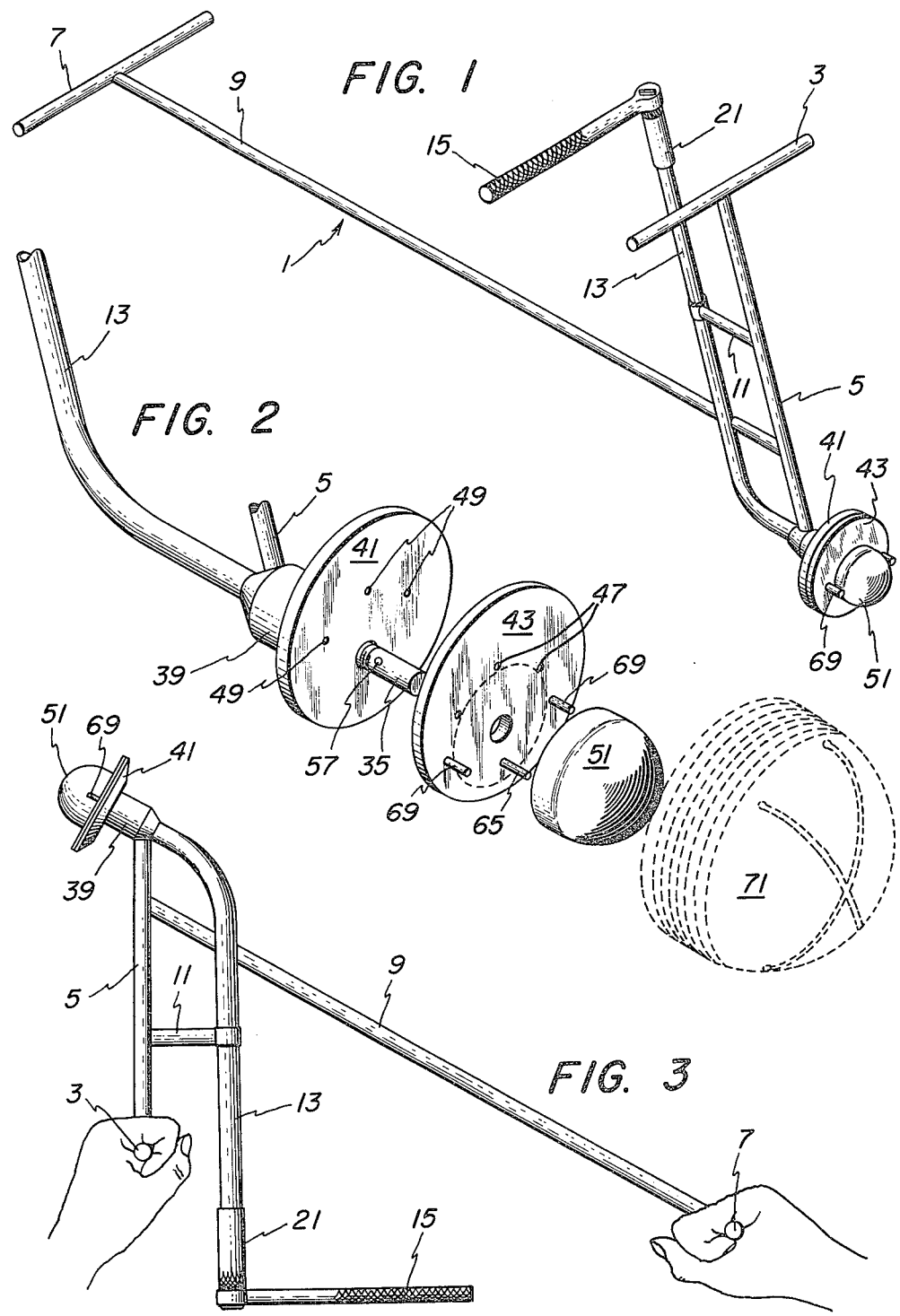

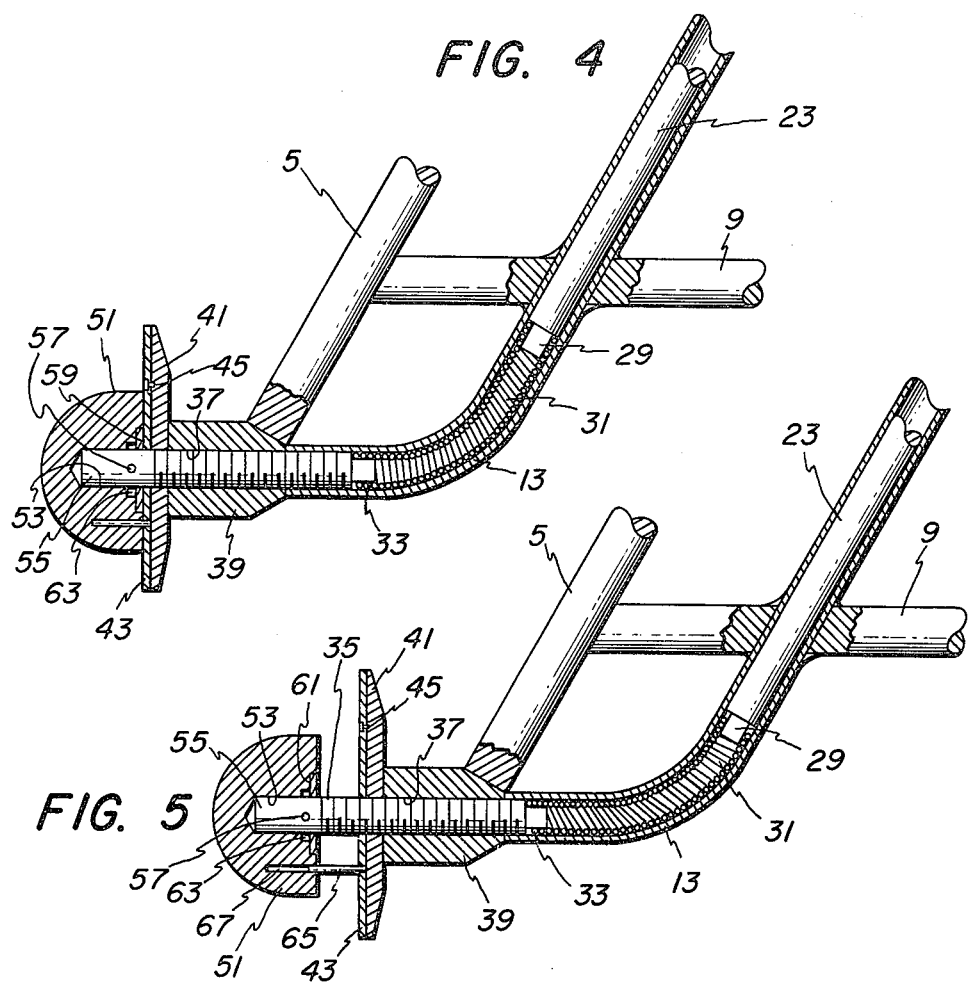
FIG. 4
FIG. 5
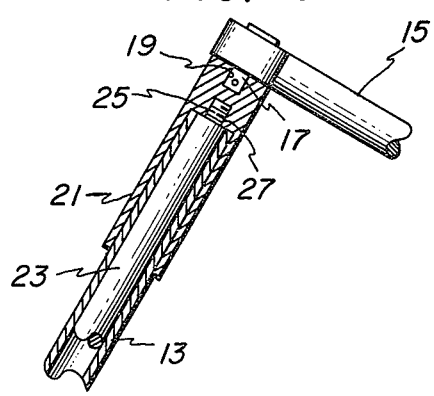
FIG. 6
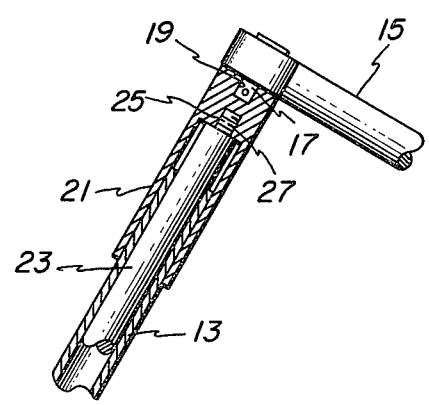
FIG. 7

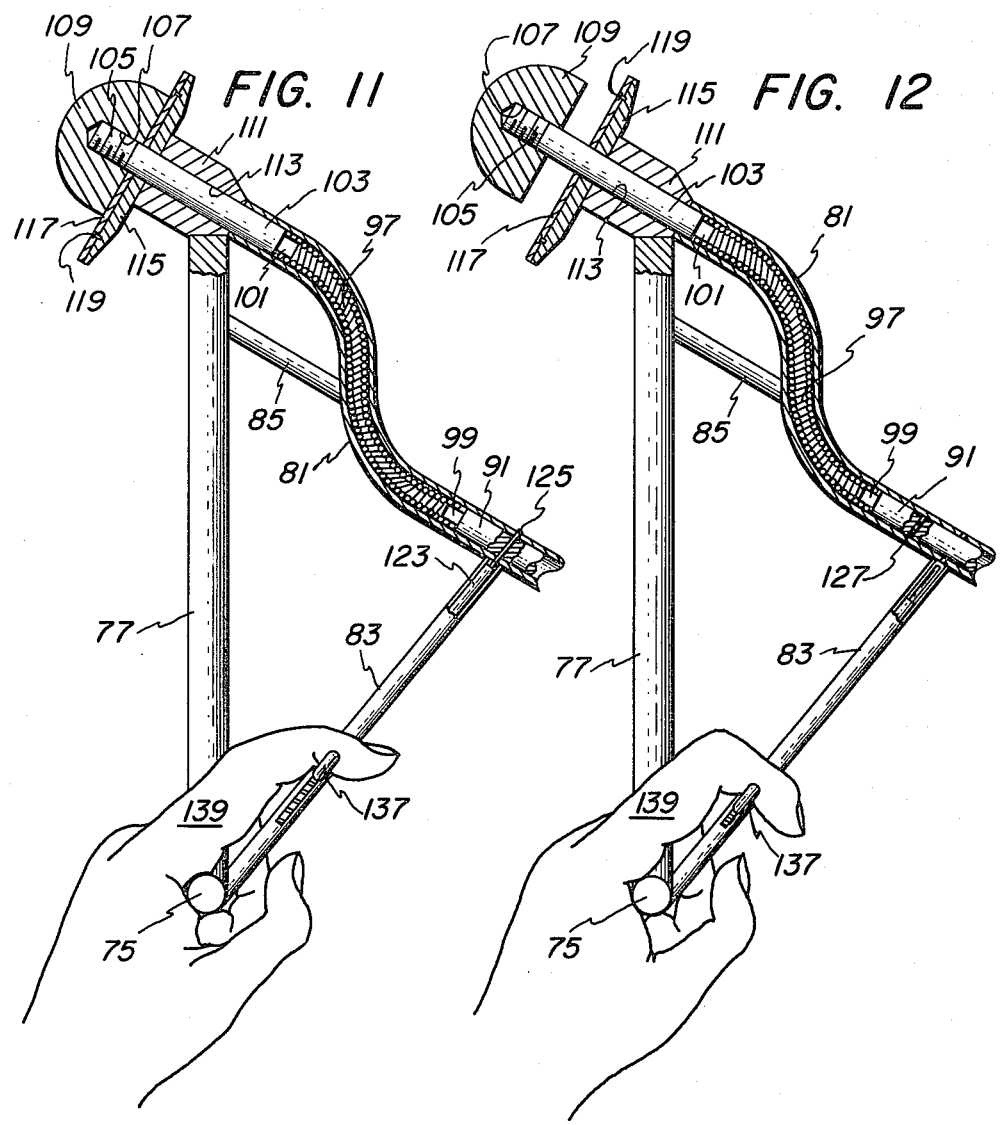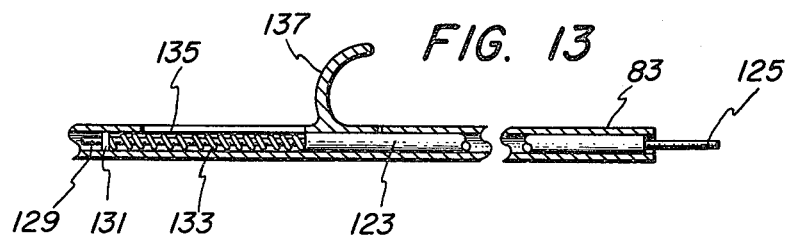

ACETABULAR CUP POSITIONING INSTRUMENT

BACKGROUND OF THE INVENTION

1. Technical Field

This invention relates generally to surgical instruments, and more particularly relates to an instrument for positioning an acetabular prosthetic cup during total hip surgery.

2. Background Art

The prior art, U.S. Pat. No. 3,859,992, discloses a vacuum-operated acetabular cup holder and positioner.

SUMMARY OF THE INVENTION

The object of the invention is to provide an acetabular cup positioning instrument for use in positioning an acetabular prosthetic cup during total hip surgery.

In the present state of the art of inserting total hip replacements in humans, the high-density polyethylene acetabular cup is held in the proper alignment with respect to the pelvis of the person being operated on by means of a cup positioner. The high-density polymethyl methacrylate cement is initially inserted into the reamed acetabulum and, at the appropriate time, the acetabular cup is pushed into place and held in the proper alignment with the cup positioner. Usually, the acetabular cup is inserted after approximately 4 to 5 minutes mixing time of the polymethyl methacrylate cement. The acetabular cup is held usually unti it is completely solid at approximately 15 minutes. Initially, when the acetabular cup is held in place with and by the cup positioner, the cement is still in a semi-fluid state. During this period of time, the acetabular cup is held firmly in place by the ball of the cup positioner and is aligned by the attached flange of the cup positioner with guide pins to properly align the acetabular cup. Some acetabular cups have eccentric holes so there will be more wear on the superior or upper portion of the cup to allow more wear, therefore, alignment holes have to be provided in the acetabular cup. But at approximately 3 to 4 minutes of holding the cup positioner with the acetabular cup in place, which is now approximately 8 minutes elapsed of combined mixing time and holding time, the polymethyl methacrylate cement is hard enough such that the continued purpose of the attached flange is no longer necessary. After this period of time, if there is any motion of the patient or any motion of the operating surgeon holding the cup positioner, any such slight motion itself will be transmitted to the acetabular cup through the attached flange for the reason that there is a long lever arm created by the two handles of the cup positioning instrument. Understandably, a small amount of motion of the operating surgeon's hands is transmitted in an amplified way by such long lever arm through such attached flange to the acetabular cup. This will allow some torquing of the acetabular cup and affect the fixation of the acetabular cup in the cement.

In the acetabular cup positioning instrument of this invention, after the interchangeable flange has served its purpose in holding the proper alignement of the acetabular cup, the interchangeable flange is disengaged from the acetabular cup while still holding longitudinal pressure against the acetabular cup with and by means of the extending interchangeable hemisphere or ball. The ball is disengaged from the interchangeable flange to the extent necessary such that the guide pins utilized to align the acetabular cup are disengaged from their associated holes in order that any motion of the operating surgeon, or any motion of the patient, will allow just the ball to rotate freely or otherwise move within the acetabular cup; and, since the interchangeable flange is no longer engaged with the rim portion of the acetabular cup, such interchangeable flange cannot transmit or otherwise force pressure along such rim portion of such acetabular cup, and, which, if otherwise were the case, would interfere with or otherwise cut down the secure fixation of the acetabular cup within the cement.

Total hip replacements are one of the most common major operations in the hip at the present time for arthritis and other diseases of the hip. It is an exceedingly lengthy operation and very costly. One of the big complications has been the loosening of the acetabular cup or the loosening of the femoral component which articulates with the acetabular cup. Understandably, this invention is a means for removing one of the described variables which may be a contributing factor in the ultimate loosening of the acetabular cup.

The revision operation for replacing a loose acetabular cup or femoral component is much lengthier than the original operation and more hazardous. Moreover, the complications of revising an acetabular cup or the femoral component are greater then the original operation. If the acetabular cup is loose, the cup along with the original cement must be removed, and there is also loss of bone stock. Such complications are very hazardous for the patient and various types of stainless steel meshes or other metallic devices have to be placed in the acetabulum to make up for this loss of bone stock.

Initially, the ball and flange of the cup positioner are adjacent to each other and directly fit in the acetabular cup. With this invention, the pressure of the ball against the cup is never released while the flange is retracted and prevented from applying a torquing force against the rim portion of the cup which will allow it to move while it should be held perfectly motionless while the cement is hardening.

The ball of the acetabular cup positioning instrument is interchangeable and a particular size ball can be utilized to fit a particular type of manufactured acetabular cup. Likewise, the flange with its guide pin or guide pins is interchangeable and, hence, a particular type of interchangeable flange can be utilized to fit a particular type of manufactured acetabular cup. Accordingly, one acetabular cup positioning instrument of this invention can be utilized with various sizes of interchangeable balls and various types of interchangeable flanges to fit all types of manufactured acetabular cups of different sizes and with different rim portions and holes receiving guide pins.

There are two embodiments of the invention. Both embodiments employ an interchangeable ball and interchangeable flange to complementally engage the acetabular prosthetic cup, with the ball engaging the inner cavity of the cup and the flange engaging the rim portion of the cup. After such prosthetic cup has been properly positioned in the patient, both embodiments employ means to disengage the flange away from the rim portion of the prosthetic cup by translatory movement of the ball away from the flange. In the one embodiment, translatory movement of the instrument ball away from the instrument flange is by means of a threaded or screw-type drive driven by a ratchet-type drive wrench through a flexible drive cable. In the other embodiment, translatory movement of the instrument ball away from the instrument flange is by means of a hand-operated push-pull cable by "squeezing" together a handle and plunger handle.

Another advantage derived from using either one of the instruments of this invention is the fact that when the flange is retracted any cement which has extruded from between the cup and the bony acetabulum, and which cement may have flowed on the outside of the flange is pulled away from the acetabular cup without jeopardy of moving the acetabular cup, and thereby allows removal of any extruded cement from around the flange. One of the problems encountered in cementing the acetabular cup with the cup positioner of the prior art is the fact that it is sometimes very difficult to see the cement which is extruded outside the flange; and, if such extruded cement hardens completely, it is extremely difficult to remove such cement. Moreover, any attempt to remove such extruded cement that has hardened by use of various instruments, may result in jeopardy to the fixation of the acetabular cup cemented to the bony acetabulum. Even if the flange is retracted and cement is left in place and allowed to harden, it is extremely easy to reunite the ball and the flange and remove the cup positioner with a hardened extruded cement. In the prior art, if cement is allowed to extrude around the flange, such cement will essentially affix the cup positioner to the acetabular cup, and such cup positioner can only be removed with much difficulty and much hazard will result to the fixation of the cup to the cement and the bony acetabulum.

BRIEF DESCRIPTION OF THE DRAWINGS

This object and other object of the invention should be discerned and appreciated by reference to the drawings, wherein like reference numerals refer to similar parts throughout the several views, in which:

FIG. 1 is an isometric view of one embodiment of the invention;

FIG. 2 is an exploded isometric view of part of the embodiment shown in FIG. 1 along with an acetabular prosthetic cup that is shown in phantom lines;

FIG. 3 is a top view of the embodiment shown in FIG. 1;

FIG. 4 is a view, partly in section, of the flange end of the embodiment of FIG. 1;

FIG. 5 is a view similar to FIG. 4 showing the translatory separation of the ball away from the flange;

FIG. 6 is a view, partly in section, of the ratchet-type drive wrench and operatively connected flexible drive cable, and corresponds to the open position or position of translatory separation of the ball away from the flange as shown in FIG. 5;

FIG. 7 is a view, partly in section, of the ratchet-type drive wrench and operatively connected flexible drive cable, and corresponds to the closed position of the ball and flange as shown in FIG. 4;

FIG. 11 is a view, partly in section, of the flange end of the embodiment of FIG. 8 and shows the locking pin engaged with the drive coupling rod;

FIG. 12 is a view similar to FIG. 11 and shows the locking pin disengaged;

FIG. 13 is an enlarged view, partly in section of the locking pin assembly.

DESCRIPTION OF THE PREFERRED EMBODIMENT

Figure 8:
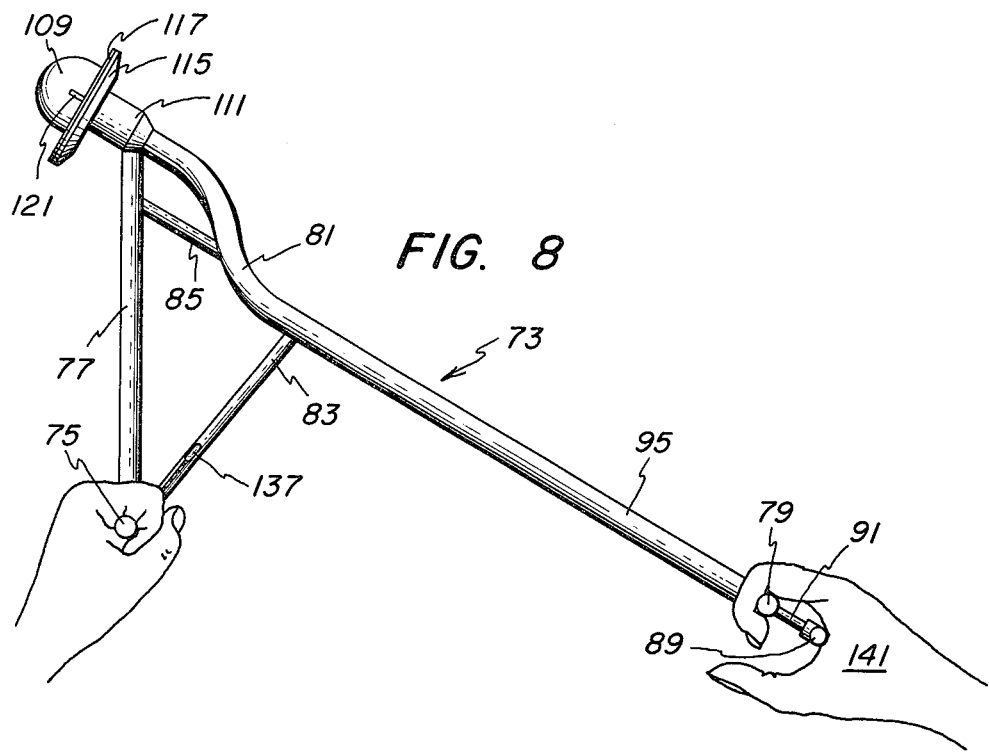
FIG. 8 is a view of another embodiment of the invention in which the translatory movement of the ball away from the flange is effected by a hand-operated push-pull cable.
Figure 9:
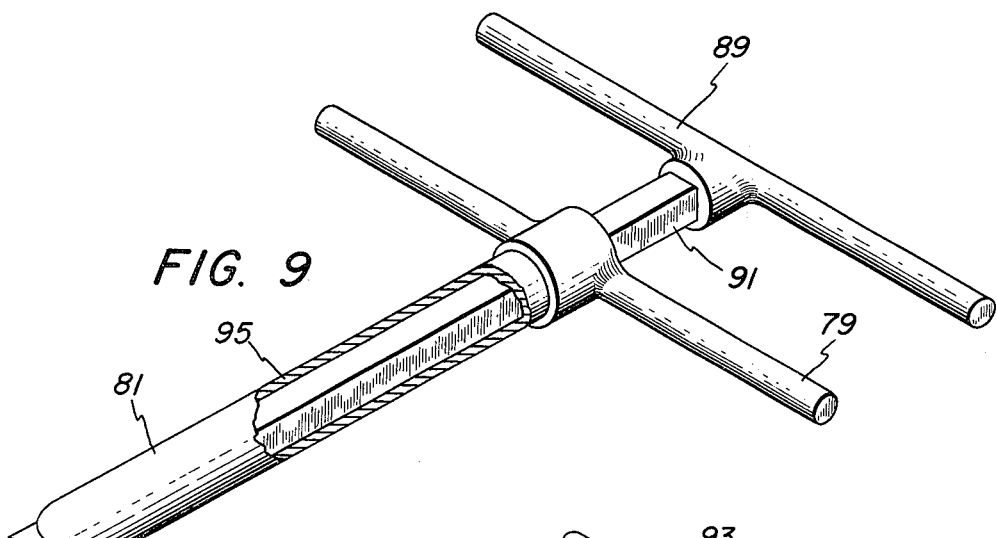
FIG. 9 is an isometric view of part of the embodiment of FIG. 8 and shows the handle end.
Figure 10:
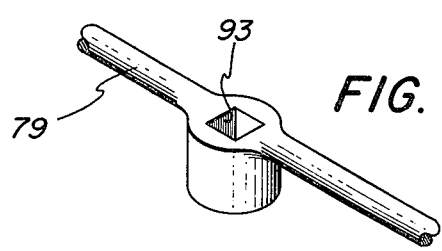
FIG. 10 is a detail of the handle.

In FIG. 1 of the drawings, reference numeral 1 generally refers to the invention of the acetabular cup positioning instrument.

Instrument 1 has a left-hand handle 3 fixed to a left-hand stabilizing rod 5, and a right-hand handle 7 fixed to a right-hand stabilizing rod 9. Fixed to and transversely extending from rod 5 is a bracket 11 which is suitably fixed to and carries an L-shaped, hollow drive housing 13. As shown, right-hand stabilizing rod 9 is suitably fixed to both left-hand stabilizing rod 5 and drive housing 13.

A conventional drive ratchet wrench 15 has its square male end 17 operatively engaged with complemental female socket 19 of coupling sleeve 21 freely mounted on drive housing 13. Freely disposed in drive housing 13 is a drive coupling rod 23 whose threaded male end 25 is operatively engaged with the tapped hole 27 of sleeve 21, and whose other end 29 is operatively connected to a flexible drive cable 31 freely disposed in housing 13. The other end 33 of drive cable 31 is operatively connected to a drive screw 35 that is operatively engaged with the tapped hole 37 formed in stationary flange support 39. As shown, the ends of rod 5 and housing 13 are suitably fixed to flange support 39.

Suitably fixed to flange support 39 is a stationary flange 41 carrying an interchangeable flange 43 by means of Allen screws 45 disposed through holes 47 in flange 43 and engaged with aligned tapped holes 49 formed in flange 41.

Freely carried on the end of drive screw 35 is an extending interchangeable hemisphere or ball 51 by means of a complemental hole 53 formed in ball 51 and receiving the end 55 of drive screw 35, and by means of a ball detent 57 disposed through the opening of a washer 59, suitably fixed in a complemental recess 61 formed in ball 51, and with such ball detent 57 being relieved within a channel 63, as shown. A stabilizing pin 65 fixed to and transversely projecting from flange 43 is received within a complemental, elongated hole 67 formed in ball 51 such that upon drive being imparted to drive screw 35, there will be translatory movement of ball 51 toward or away from flange 43 but without any rotation of ball 51.

Transversely projecting from flange 43 are guide pins 69 which are adapted to be received by and within corresponding, complemental holes in the acetabular prosthetic cup 71 shown in phantom lines in FIG. 2.

Cup 71 is of high-density polyethylene material. The front, convex outer portion of cup 71 is appropriately disposed in the patient's reamed and prepared acetabulum. Ball 51 of instrument 1 complementally mates with the inner cavity of cup 41. The rearward-most portion of cup 71 between its said outer portion and inner cavity defines a rim portion or planar flange with which flange 43 complementally abuts and mates. Cup 71 has holes which correspond with and complementally receive therein the guide pins 69 transversely projecting from flange 43 in order to precisely orient and align instrument 1 relative to cup 71 in order that cup 71 may thereafter be properly disposed in the patient's acetabulum.

It should be appreciated that the acetabular cups 71 manufactured have various sizes, inner cavities, rim portions or planar flanges, and one or more holes which complementally receive one or more guide pins 69.

Since both the flange 43 and ball 51 are interchangeable, a particular size and type of flange 43 with the required guide pin or guide pins 69 can be secured to stationary flange 41 as was heretofore described, and a particular size and type ball 51 can be secured with drive screw 35 as was heretofore described.

The cup positioning instrument 1, shown in FIGS. 1 through 7, and as has been described herein, is utilized as has been described in the "Summary of the Invention" to appropriately dispose cup 71 in the patient's reamed and prepared acetabulum.

In this connection, the particular flange 43 and ball 51 required for the particular size and type cup 71 are operatively disposed and engaged with cup 71 such that flange 43 is in mating relationship with the rim portion of cup 71, such that the guide pin or guide pins 69 are disposed within the corresponding hole or holes in cup 71 to precisely orient and align instrument 1 with respect to cup 71, and such that ball 51 complementally mates with the inner cavity of cup 71. When it is desired to disengage flange 43 from the rim portion of cup 71, and to disengage the guide pin or pins 69 from the hole or holes in cup 71 which correspondingly and complementally received same, ratchet-type drive wrench 15 is appropriately manipulated to the extent necessary to transmit sufficient drive to drive screw 35 to effect the desired and required translatory movement of ball 51 away from flange 43.

In the other embodiment of the instrument shown in FIGS. 8 through 13, reference numeral 73 in FIG. 8 generally refers to the invention.

Instrument 73 has a left-hand handle 75 fixed to a left-hand stabilizing rod 77, and a right-hand handle 79 fixed to a serpentine-shaped drive housing 81. Suitably fixed to left-hand stabilizing rod 77 and drive housing 81 is a locking-pin assembly housing 83, and suitably fixed to left-hand stabilizing rod 77 and drive housing 81 is a support bracket 85. Right-hand handle 79 is suitably fixed to drive housing 81 which acts similar to right hand stabilizing rod 9.

Plunger handle 89 is suitably fixed to a square-shaped drive coupling rod 91 complementally received by the square-shaped hole 93 of handle 79. Coupling rod 91 is freely disposed in the rectilinear portion 95 of drive housing 81. Flexible drive cable 97 is freely disposed in drive housing 81 and has one end suitably fixed to the other end 99 of drive coupling rod 91, and drive cable 97 has its other end suitably fixed to the one end 101 of a drive rod 103. The other end 105 of drive rod 103 is threaded and is engaged with a tapped hole 107 in extending interchangeable hemisphere or ball 109 to fixedly carry ball 109 thereby.

As shown, the ends of stabilizing rod 77 and drive housing 81 are suitably fixed to a stationary flange support 111 which has a hole 113 complementally receiving therethrough drive rod 103. Suitably fixed to flange support 111 is a stationary flange 115 carrying an interchangeable flange 117 by means of Allen screws 119, and similar to the securement of flange 43 with stationary flange 41 by means of Allen screws 45.

Transversely projecting from interchangeable flange 117 are one or more guide pins 121 which are adapted to be received by and within corresponding, complemental holes in the acetabular prosthetic cup 71.

Locking-pin assembly housing 83 freely and complementally receives therein a locking pin rod 123 having on one end a locking pin 125 engageable through a hole in housing 81 with an aligned hole 127 formed in drive coupling rod 91 to prevent movement of rod 91. The other end of locking pin rod 123 has a reduced rod portion 129 freely and complementally received within a hole in shoulder 131 fixed within housing 83. A compression spring 133, mounted as shown on rod portion 129, biases locking pin 125 into locking engagement with hole 127. Integral with and upstanding from locking pin rod 123, and guided by a complemental guide slot 135 formed in housing 83, is a trigger 137. FIG. 11 shows locking pin 125 in its locking engagement with aligned hole 127 of coupling rod 91.

In similar fashion to ball 51, ball 109 likewise complementally mates with the inner cavity of cup 71. In similar fashion to flange 43, flange 117 complementally mates with the rim portion of cup 71. Cup 71 has holes which correspond with and complementally receive therein the guide pins 121 transversely projecting from flange 117 in order to precisely orient and align instrument 73 relative to cup 71 in order that cup 71 may thereafter be properly disposed in the patient's acetabulum.

As stated previously with reference to instrument 1, it should similarly be discerned and appreciated that the acetabular cups 71 manufactured have various sizes, inner cavities, rim portions or planar flanges, and one or more holes which complementally receive one or more guide pins 121. Since both the ball 109 and flange 117 are interchangeable, a particular size and type of flange 117 with the required guide pin or guide pins 121 can be secured to stationary flange 111 as heretofore described, and a particular size and type ball 109 can be fixed to the threaded end 105 of drive rod 103 as heretofore described.

The cup positioning instrument 73, shown in FIGS. 8 through 13, and as has been described herein, is utilized as has been described in the "Summary of the Invention" to appropriately dispose cup 71 in the patient's reamed and prepared acetabulum.

In this connection, the particular flange 117 and ball 109 required for the particular size and type cup 71 with which they are to be utilized are operatively disposed and engaged with cup 71 such that flange 117 is in mating relationship with the rim portion of cup 71, such that guide pin or guide pins 121 are disposed within the corresponding hole or holes in cup 71 to precisely orient and align instrument 73 with respect to cup 71, and such that ball 109 complementally mates with the inner cavity of cup 71. When it is desired to disengage flange 117 from the rim portion of cup 71 and to disengage the guide pin or guide pins 121 from the holes in cup 71 which correspondingly and complementally received same, trigger 137 is appropriately manipulated with one's left index finger 139 to thereby release locking pin 125 from its biased locking engagement with hole 127 in drive coupling rod 91 so that drive coupling rod 91 can be moved freely within housing 83, and at the same time one's right hand 141 is appropriately disposed about the right-hand handle 79 and plunger handle 89 as shown in FIG. 8 with one thereupon "squeezing" his right hand 141 together to thereby move drive rod 103 and hence ball 109 outwardly to effect the desired and required translatory movement of ball 109 away from flange 117.

Having thusly described my invention, I claim:

1. An instrument of integral construction for positioning an acetabular prosthetic cup during surgery, said acetabular prosthetic cup having an inner cavity and a rim portion, said instrument comprising a ball and a flange for mounting, orienting and aligning said acetabular prosthetic cup relative to said instrument, a left hand handle fixed to a left hand stabilizing rod, a right hand handle fixed to a right hand stabilizing rod, said stabilizing rods connected to each other at an angle and supporting said ball and flange, said ball and flange so sized and shaped as to complementally engage said acetabular prosthetic cup with said ball complementally mating with said inner cavity of said acetabular prosthetic cup and said flange engaging said rim portion of said acetabular prosthetic cup, and means for disengaging said instrument's flange away from sid rim portion of said acetabular prosthetic cup while said ball maintains engagement with said prosthetic acetabular cup and while longitudinal axial pressure on said acetabular prosthetic cup by said ball is maintained throughout substantially the entire area of said inner cavity.

2. An instrument in accordance with claim 1, wherein said means for disengaging said instrument's flange away from said rim portion comprises means for moving said instrument's ball away from said instrument's flange while said ball maintains engagement with said acetabular cup.

3. An instrument in accordance with claim 1, wherein said means for disengaging said instrument's flange away from said rim portion comprises means for effecting translatory movement of said instrument's ball away from said instrument's flange while said ball maintains engagement with said acetabular cup.

4. An instrument in accordance with claim 1, wherein said ball and flange are interchangeable with a particular size and type ball and flange to mount, orient and align said acetabular cup wherein said acetabular cup correspondingly is of such particular size and type.

5. An instrument in accordance with claim 4, wherein said instrument has a stationary flange support and a stationary flange, wherein said stationary flange support carries said stationary flange, and wherein said stationary flange carries said interchangeable flange.

6. An instrument in accordance with claim 1, wherein said acetabular cup has a hole, wherein said flange has a guide pin and wherein said hole in said acetabular cup correspondingly and complementally receives said guide pin to cooperatively mount, orient and align said acetabular cup.

7. An instrument in accordance with claim 1, wherein said acetabular cup has holes, wherein said flange has guide pins and wherein said holes in said acetabular cup correspondingly and complementally receive said guide pins to cooperatively mount, orient and align said acetabular cup.

8. An instrument in accordance with claim 1, wherein said means for disengaging said instrument's flange away from said rim portion of said acetabular cup comprises flexible drive means operatively connected to said ball and wherein, upon appropriate drive being imparted to said flexible drive means, said flexible drive means moves said ball carrying said acetabular cup away from said flange.

9. An instrument in accordance with claim 8, wherein said instrument has a screw-type drive means and wherein said screw-type drive means operatively connects said flexible drive means to said ball.

10. An instrument in accordance with claim 8, wherein said instrument has a drive wrench and wherein, upon appropriate operative engagement of said drive wrench with said flexible drive means, said drive wrench imparts drive to said flexible drive means.

11. An instrument in accordance with claim 8, wherein said instrument ha a screw-type drive means and a drive wrench, wherein said screw type drive means operatively connects said flexible drive means to said ball, and wherein, upon appropriate operative engagement of said drive wrench with said flexible drive means, said drive wrench imparts drive to said flexible drive means.

12. An instrument in accordance with claim 8, wherein said right hand handle is a plunger handle, wherein said plunger handle is operatively connected to said flexible drive means, and, wherein, upon appropriate inward movement of said plunger handle, said flexible drives means moves said ball away from said flange.

13. An instrument in accordance with claim 8, wherein said right hand handle is a plunger handle and a handle, wherein said plunger handle is operatively connected to said flexible drive means, and wherein, upon said plunger handle and said handle being "squeezed" together, said plunger handle imparts inward movement to said flexible drive means to move said ball away from said flange.

14. An instrument in accordance with claim 8, wherein said right hand handle is a plunger handle, wherein said plunger handle is connected to a drive coupling rod, wherein said drive coupling rod is operatively connected to said flexible drive means, and, wherein, upon appropriate inward movement of said plunger handle, said flexible drive means moves said ball away from said flange.

15. An instrument in accordance with claim 14, wherein said instrument has a locking-pin means and wherein said locking-pin means is releasably engaged with said drive coupling rod to prevent movement of said drive coupling rod.

16. An instrument in accordance with claim 1, wherein said means for disengaging said instrument's flange away from said rim portion of said cup while said ball maintains engagement with said acetabular cup comprises a drive wrench, coupling sleeve, drive coupling rod, flexible drive cable, drive screw and stationary flange support, wherein said coupling sleeve operatively connects said drive wrench to said drive coupling rod, wherein said flexible drive cable operatively connects said drive coupling rod to said drive screw, wherein said stationary flange support has a tapped hole, wherein said drive screw operatively engages said tapped hole of said stationary flange support, wherein said drive screw carries said ball, and, wherein, upon appropriate operative engagement of said drive wrench, drive is transmitted to said drive screw.

17. An instrument in accordance with claim 16, wherein said drive screw has a ball detent, wherein said ball has a hole and a channel, wherein said drive screw removably carries said ball by said hole in said ball complementally receiving said drive screw and by said ball detent being relieved in said channel of said ball.

18. An instrument in accordance with claim 16, wherein said flange has a stabilizing pin, wherein said ball has an elongated hole, and wherein said elongated hole of said ball complementally receives said stabilizing pin of said flange to prevent rotation of said ball upon drive being imparted to said drive screw.

19. An instrument in accordance with claim 16, wherein said drive screw has a ball detent, wherein said ball has a hole and a channel, wherein said drive screw removably carries said ball by said hole in said ball complementally receiving said drive screw and by said ball detent being relieved in said channel of said ball, and wherein said flange has a stabilizing pin, wherein said ball has an elongated hole, and wherein said elongated hole of said ball complementally receives said stabilizing pin of said flange to prevent rotation of said ball upon drive being imparted to said drive screw.

20. An instrument in accordance with claim 16, wherein said instrument has a drive housing, wherein said drive housing carries said coupling sleeve, wherein said drive housing freely receives said drive coupling rod and flexible drive cable.

21. An instrument in accordance with claim 1, wherein said means for disengaging said instrument's flange away from said rim portion of said cup while said ball maintains engagement with said acetabular cup comprises said right hand handle which is a plunger handle, a drive coupling rod, a flexible drive cable and a drive rod, wherein said plunger handle carries said drive coupling rod, wherein said flexible drive cable operatively connects said drive coupling rod to said drive rod, wherein said drive rod carries said ball, and, wherein, upon appropriate inward movement of said plunger handle, drive is transmitted to said drive rod to move said ball away from said flange.

22. An instrument in accordance with claim 21, wherein said ball has a tapped hole, wherein said drive rod has a threaded end, and wherein said drive rod removably carries said ball by said threaded end of said drive rod being engaged with said tapped hole of said ball.

23. An instrument in accordance with claim 21, wherein said instrument has a locking-pin means and wherein said locking-pin means is releasably engaged with said drive coupling rod to prevent any drive from being transmitted to said drive rod.

24. An instrument in accordance with claim 21, wherein said instrument has a drive housing, wherein said drive housing freely receives said drive coupling rod and said flexible drive cable.

25. An instrument in accordance with claim 24, wherein said drive housing carries a handle, and wherein said plunger handle and handle are "squeezed" together to effect said appropriate inward movement of said plunger handle.

* * * * *